United States Patent
Cao et al.

(10) Patent No.: US 8,856,158 B2
(45) Date of Patent: Oct. 7, 2014

(54) SECURED SEARCHING

(75) Inventors: Feng Cao, Beijing (CN); Chen Yang Wu, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/596,127

(22) Filed: Aug. 28, 2012

(65) Prior Publication Data

US 2013/0054554 A1   Feb. 28, 2013

(30) Foreign Application Priority Data

Aug. 31, 2011   (CN) .......................... 2011 1 0253462

(51) Int. Cl.
*G06F 17/30* (2006.01)
*G06F 21/62* (2013.01)

(52) U.S. Cl.
CPC .......... *G06F 17/30* (2013.01); *G06F 17/30536* (2013.01); *G06F 21/6254* (2013.01)
USPC ............................................. 707/757; 726/26

(58) Field of Classification Search
CPC ....................... G06F 17/30536; G06F 21/6254
USPC ............................................. 707/757; 726/26
See application file for complete search history.

(56) References Cited

U.S. PATENT DOCUMENTS

| | | | |
|---|---|---|---|
| 5,961,593 A | 10/1999 | Gabber et al. | |
| 6,253,203 B1 | 6/2001 | O'Flaherty et al. | |
| 7,630,986 B1 | 12/2009 | Herz et al. | |
| 7,752,215 B2 | 7/2010 | Dettinger et al. | |
| 2007/0061335 A1 | 3/2007 | Ramer et al. | |
| 2007/0178501 A1 | 8/2007 | Rabinowitz et al. | |
| 2009/0172773 A1 | 7/2009 | Moore | |
| 2010/0005091 A1* | 1/2010 | Bayliss | 707/5 |

OTHER PUBLICATIONS

Beck, et al. (Apr. 2008). Weighted boolean conditions for ranking. In Data Engineering Workshop, 2008. ICDEW 2008. IEEE 24th International Conference on (pp. 568-571). IEEE.*
Machanavajjhala, et al. (2007). I-diversity Privacy beyond k-anonymity. ACM Transactions on Knowledge Discovery from Data.*
Xiao, et al. Anatomy Simple and effective privacy preservation. Proceedings of the 32nd international conference on Very large data bases. VLDB Endowment, 2006.*
IBM, Selectivity of predicates, 2006.*
Emecki et al.,"Privacy Preserving Query Processing Using Third Parties," Data Engineering, 2006. ICDE '06. Proc. of the 22nd International Conference on, pp. 27, 03-07, 2006.
Chen et al., "Privacy-Preserving Data Publishing," Journal Foundations and Trends in Databases, archive, vol. 2, Issue 1-2, Jan. 2009, pp. 1-167.
Singh et al., "Overview of Top-K Query Processing in Relational Databases," International Journal of Enterprise Computing and Business Systems, vol. 1, Issue 2, 2011, pp. 1-9.
Yuan et al., "Personalized privacy protection in social networks," Proceedings of the VLDB Endowment, vol. 4, No. 2, pp. 141-150, Nov. 2010.

* cited by examiner

*Primary Examiner* — William Spieler
(74) *Attorney, Agent, or Firm* — Stephen R. Yoder

(57) ABSTRACT

A method and system for a secured search. The method includes the steps of: receiving a search request from a searching user; determining search results to be returned to the searching user based on a security schema; and returning the search results to the searching user, where at least one of the steps is carried out by using a computer device.

15 Claims, 7 Drawing Sheets

SECURED SEARCHING

CROSS-REFERENCE TO RELATED APPLICATION

This application claims priority under 35 U.S.C. §119 from Chinese Patent Application No. 201110253462.0 filed Aug. 31, 2011, the entire contents of which are incorporated herein by reference.

BACKGROUND OF THE INVENTION

1. Field of the Invention

The present invention relates to information processing. More specifically, the present invention relates to a method and device for a secured search.

2. Description of Related Art

Cloud computing is a service delivery model that provides convenient and on-demand network access to configurable shared computing resource pool. With the popularization of cloud computing, more people are encouraged to store and manage their information via the Internet. Users who manage their information through cloud computing are called as cloud consumers. For example, many cloud consumers taking advantage of cloud computing have emerged in the medical field, which includes websites such as PatientsLikeMe and Google health.

From the perspective of network resource utilization, websites such as PatientsLikeMe desires user (e.g. patient) information shared with other public individuals. However, people always want to preserve their privacy. According to a research in 2008, 25% of the participants chose to provide fake information when accessing a website, because 72% of the participants are concerned that their online information and behavior can be tracked and used by service providers, particularly in the medical field. The well-known medical website PatientsLikeMe encourages transparency of medical privacy to provide better healthcare service.

One approach to address this abovementioned problem uses information anonymization. In the information anonymization method, data are rewritten with generalization, suppression or perturbation, and other manners, in order to break the integrity of individuals' information while maintaining the features of the whole dataset. However, anonymized data generated in this method is preferred by research institutions rather than public individuals, because, after such perturbation, some types of information are unable to provide reasonable suggestions.

Another possible approach is a secured search. For example, users' sensitive data is encrypted. User sensitive data are generally invisible to searching users in search results, and a common searching user only can visit non-sensitive user data. Further, searchable encryption and index allow Information sharing. Thus, a searching user can access other users' whole data with those users' permission. However, this approach prevents effective information sharing, because permission from the users can render search results completely visible or invisible.

In view of the prior art, it is desired to provide a technique capable of realizing user information sharing to a greater extent while preserving user privacy.

SUMMARY OF THE INVENTION

Accordingly, one aspect of the present invention provides a method for a secured search, including the steps of: receiving a search request from a searching user; determining search results to be returned to the searching user based on a security schema; and returning the search results to the searching user, where at least one of the steps is carried out by using a computer device.

Another aspect of the present invention provides a secured search device, including: a search engine configured to receive a search request from a searching user; and a search result determining unit configured to determine search results to be returned to the searching user based on a security schema, where the search engine is further configured to return the search results determined by the search result determining unit to the searching user.

DETAILED DESCRIPTION OF THE PREFERRED EMBODIMENTS

Figure 1:
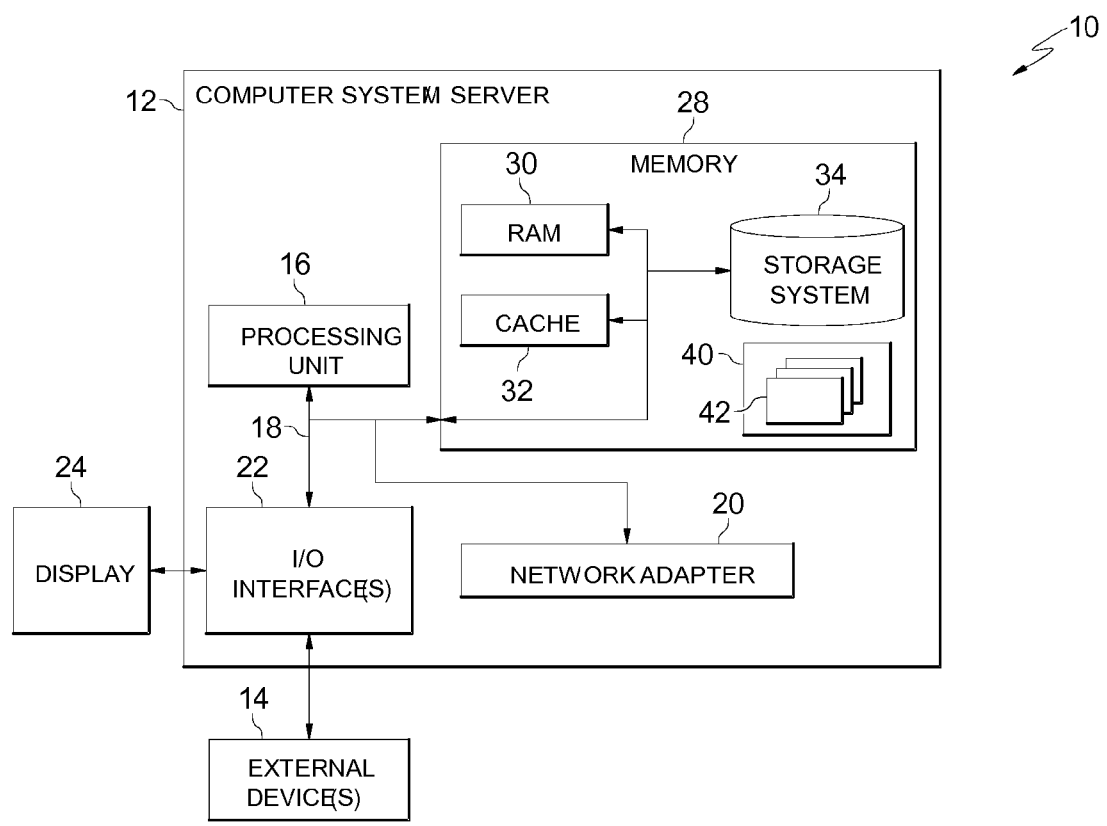
FIG. 1 shows a cloud computing node according to an embodiment of the present invention.

In the following discussion, a great amount of concrete details are provided to help thoroughly understand the present invention. However, it is apparent to those of ordinary skill in the art that even though there are no such concrete details, the understanding of the present invention can not be influenced. In addition, it should be further appreciated that any specific terms used below are only for the convenience of description, and thus the present invention should not be limited to only use in any specific applications represented and/or implied by such terms.

Further, the drawings referenced in the present application are only used to exemplify typical embodiments of the present invention and should not be considered to be limiting the scope of the present invention.

It is understood in advance that although the present disclosure includes a detailed description on cloud computing, implementation of the teachings recited herein are not limited to a cloud computing environment. Rather, embodiments of the present invention are capable of being implemented in conjunction with any other type of computing environment now known or later developed.

One problem to be solved in one embodiment of the present invention is to share user information to a greater extent while preserving user privacy.

A method for secured search is provided in one embodiment of the present invention, which can include: receiving a search request from a searching user; determining search results to be returned to the searching user based on a security schema; and returning the search results to the searching user.

A secured search device is provided in another embodiment of the present invention, which can include: a search engine configured to receive a search request from a searching user; and a search result determining unit configured to determine search results to be returned to the searching user based on a security schema; wherein the search engine is further configured to return the search results determined by the search result determining unit to the searching user.

A computer device is provided in still another embodiment of the present invention, which can include the above-mentioned secured search device.

As such, the present invention can realize user information sharing to a greater extent while preserving user privacy.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10, there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 1, computer system/server 12 in cloud computing node 10 is shown in the form of a general-purpose computing device. The components of computer system/ server 12 can include, but are not limited to, one or more processors or processing units 16, a system memory 28, and a bus 18 that couples various system components including system memory 28 and processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA bus, Video Electronics Standards Association (VESA) local bus, and Peripheral Component Interconnects (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software modules can be used in conjunction with computer system/server 12. Examples, include, but are not limited to: microcode, device drivers, redundant processing units, external disk drive arrays, RAID systems, tape drives, and data archival storage systems, etc.

Figure 2:
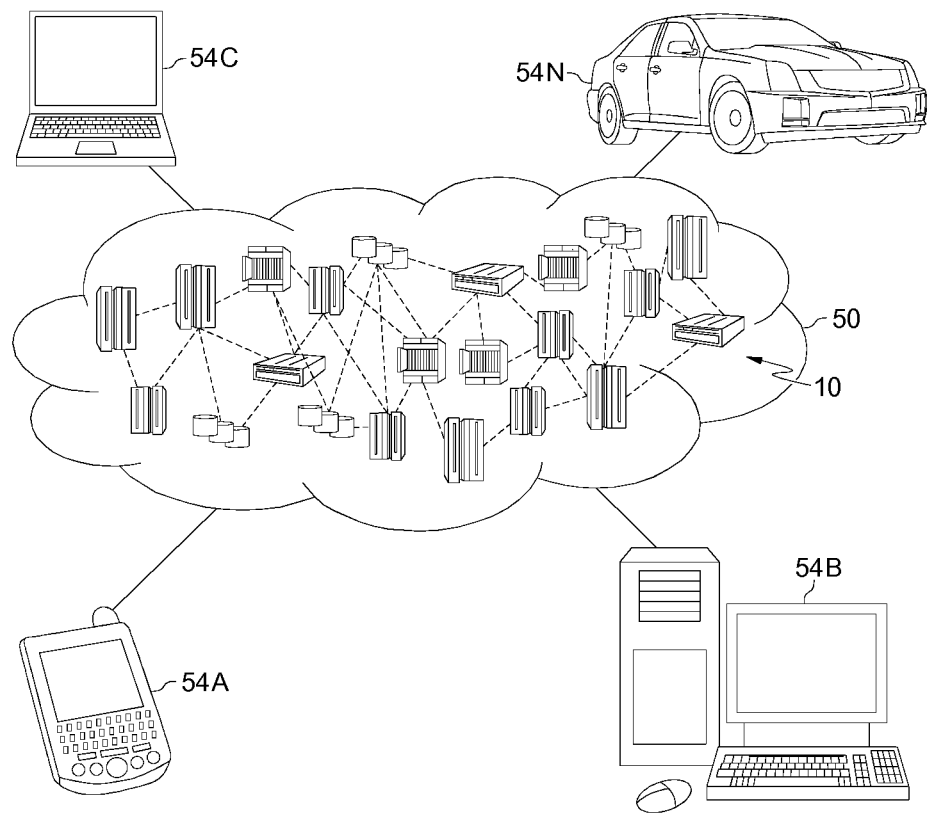
FIG. 2 shows a cloud computing environment according to an embodiment of the present invention.

Referring now to FIG. 2, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
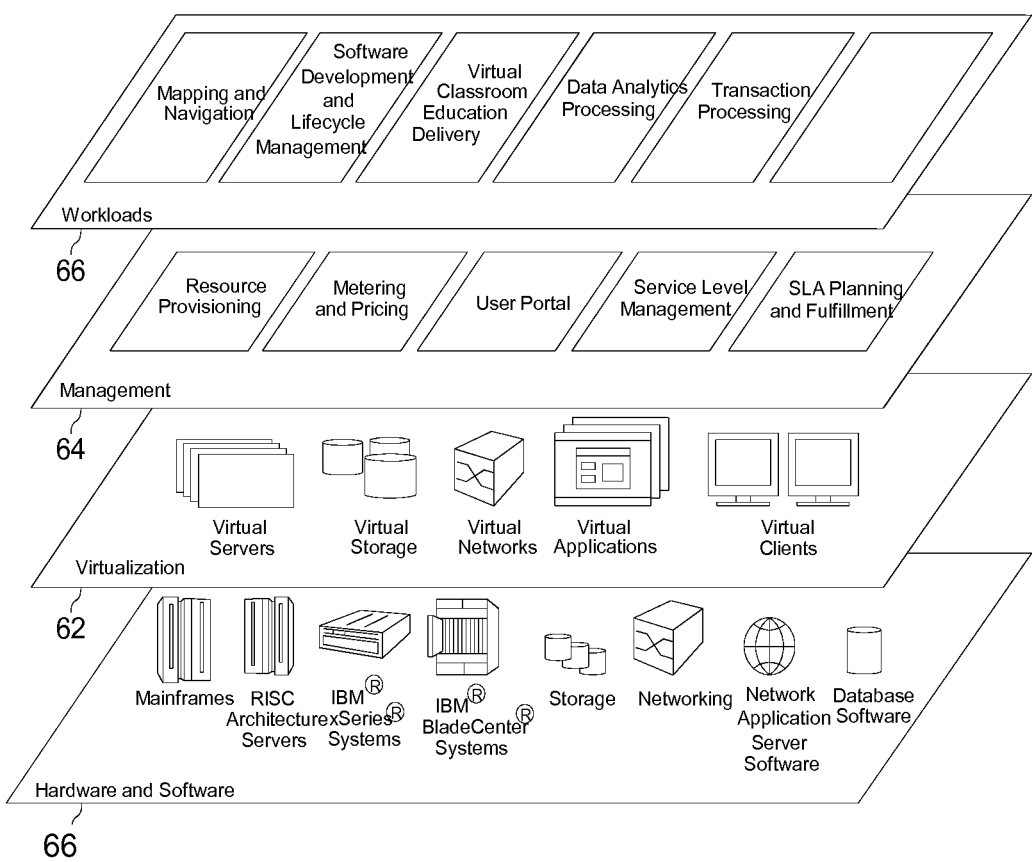
FIG. 3 shows abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities can be provided: virtual servers; virtual storage; virtual networks, including virtual private networks; virtual applications and operating systems; and virtual clients.

In one example, management layer 64 can provide the functions described below. Resource provisioning provides dynamic procurement of computing resources and other resources that are utilized to perform tasks within the cloud computing environment. Metering and Pricing provide cost tracking as resources are utilized within the cloud computing environment, and billing and invoicing for consumption of these resources. In one example, these resources can include application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer 66 provides examples of functionality for which the cloud computing environment can be utilized.

Examples of workloads and functions which can be provided from this layer include: mapping and navigation; software development and lifecycle management; virtual classroom education delivery; data analytics processing; transaction processing; and secured search implemented such as in the present invention.

The main idea of the present invention is that, instead of hiding all sensitive information as in the prior art to completely prevent any information from being accessed without authorization from the owners of the sensitive information, sensitive information can be transformed into a more generalized form according to a security schema. For example, each information owner can specify a privacy ratio, that is, a privacy level to his information. Sensitive information will be transformed into a more generalized form according to that privacy level. As another example, some established privacy levels can be employed, that is, some specific privacy levels can be adopted for some users, and other privacy levels can be utilized for others, and sensitive information will be transformed into a more generalized form according to the privacy levels. Such sensitive information can be shared by other users in generalized condition, without compromising the privacy of sensitive data at the same time. For example, a patient has got type 1 pneumonia, however, according to a desired privacy level of that patient, this information can be transformed into "pneumonia", "pulmonary disease" or "disease", and this kind of transformation can be called as generalization. Thereby, it is possible to allow searching users to get some information while preventing that patient's privacy from being revealed. That is, what users see are "views" of other information owners' sensitive data rendered in different privacy requirements. Information owners can change their privacy levels for any sensitive data, dataset can change too, leading to different views on the same piece of sensitive data. In this way, information sharing can be maximized and personalized privacy requirements of information owners can be satisfied at the same time.

That is, after receiving a search request from a searching user, instead of directly querying and returning search results to the searching user, search results to be returned to that searching user are determined based on a security schema for returning to that searching user.

In one embodiment, determining search results to be returned to that searching user based on a security schema includes generalizing the values of the attributes of the tuples in the search results to form the search results to be returned to that searching user.

In a structural data storage structure, namely, in a relational database, data are commonly stored in the form of two dimensional tables, wherein each row in a table is a relational tuple and each column is a relational attribute. For example:

| Patient | sex | age | Disease |
|---|---|---|---|
| A | male | 25 | Type 1 pneumonia |
| B | female | 45 | emphysema |

"patient A, male, 25, Type 1 pneumonia" is a tuple, and the ages of patients A and B form a relational attribute.

One manner of generalizing the values of the attributes in the tuples of the search results is: transforming a value of an attribute in a tuple of a search result into a generalized value based on a privacy ratio, wherein the value of the attribute is a subclass of the generalized value, and the ratio of the probability of finding the original tuple according to the generalized value and the probability of finding the original tuple according to the value of the attribute is less than or equal to the privacy ratio.

Referring to the above example again, it is supposed that "patient A, male, 25, Type 1 pneumonia", "patient B, female, 45, emphysema" are original tuples. Furthermore, it is assumed that there are only two persons with type 1 pneumonia in the database. Thereby, the probability of finding patient A in the database with knowledge that there is someone with type 1 pneumonia is 50%. That is, patient A can be found at a probability of 50% according to "type 1 pneumonia". However, if there are 20 persons with "pneumonia" in the database, then patient A can be found according to "pneumonia" at a probability of 5%. If patient A has specified a privacy ratio of 10% for himself, substituting "pneumonia" for "type 1 pneumonia" can lead to a ratio of the 5% probability of finding a specific tuple in which the original data "type 1 pneumonia" is contained according to the generalized data "pneumonia" and the 50% probability of finding the specific tuple according to the original data "type 1 pneumonia" less than or equal to the privacy ratio, thus, satisfying patient A's privacy requirements.

However, if patient A has specified a privacy ratio of 8%, the ratio calculated as such is 10%, which is larger than the privacy ratio. Thus, it is required to generalize "type 1 pneumonia" to "pneumonia", "respiratory disease" and the like, so that the ratio can be lowered to less than or equal to the privacy ratio.

Certainly, original data also can be generalized to generalized data through other manners occurred to those skilled in the art benefited from the above teachings. For example, instead of privacy ratios, well defined privacy levels can be employed and how each privacy level is generalized can be specified in detailed. For example, assuming four privacy levels A, B, C and D, if patient A selects privacy level D, it means that no generalization is implemented, namely, no secrecy is required. Thus, the value of the attribute "disease" in that tuple is kept as "type 1 pneumonia". If patient A selects privacy level C, "type 1 pneumonia" will be generalized to a direct upper level, that is, "pneumonia". "type 1 pneumonia" will be generalized by two levels above, that is, to "pulmonary disease" if patient A selects privacy level B, and will be generalized by three levels above, that is, to "respiratory disease" if patient A selects privacy level A.

Due to the present of the above generalization, when returning query results to a searching user, not only results accurately matching the search conditions, but also other results not completely matching but relative to the search conditions should be returned. For example, when a search condition is "disease=type 1 pneumonia", not only search results having "type 1 pneumonia" present exactly, but also search results containing "pneumonia" or "pulmonary disease" should be returned, because these results can be generalized from "type 1 pneumonia". Certainly, some search results containing "pneumonia" or "pulmonary disease" can be generalized from "type 2 pneumonia", "emphysema", and search results generated as such are not that results actually required by searching users. Therefore, a concept of similarity is introduced, by which searching users can estimate how approximately those search results reflect their actual intentions.

Optionally, when returning a search result to a searching user, its average similarity is returned to the searching user, wherein the average similarity is the average of the similarity values between the search result and each of the query conditions.

In the case of representing structural data with a tree structure, when two values of attribute (e.g. "disease=type 1 pneumonia" and "disease=pneumonia") have ancestor-descendant relationship, the similarity between two values of attributes is the coverage ratio of the two values of attributes. Coverage means herein how many tuples have that attribute with that value or subclasses of that value in a database. Given that pneumonia includes type 1 pneumonia and type 2 pneumonia, "type 1 pneumonia" and "type 2 pneumonia" are subclasses of pneumonia. For example, there are 2 persons having type 1 pneumonia and 18 persons having type 2 pneumonia in the database, the coverage of "pneumonia" is 20, the coverage of "type 1 pneumonia" is 2, and the coverage of "type 2 pneumonia" is 18. For a query condition, a coverage ratio can be calculated based on the value of an attribute in the query condition and the value of the corresponding attribute in a search result. If a search result returned against a query condition "disease=type 1 pneumonia" is "pneumonia", with respect to the query condition "disease=type 1 pneumonia", the similarity between that search result and the query condition is 2/20=10%.

When there is not ancestor-descendant relationship between two values of attributes, it is also possible to have a similarity between the two values, for example, "disease=endocrine dyscrasia" and "disease=nephropathy", since some nephropathies occur due to endocrine dyscrasia. In this situation, the similarity between the two values of attributes can be obtained through calculating the similarity values between these two values of attributes and the closest common ancestor thereof respectively, and then evaluating a harmonic average of these similarity values.

After obtaining the similarity values between the search result and each of the query conditions, the average similarity can be obtained through averaging the similarity values between the search result and each of the query conditions.

For example, a searching user inputs two conditions in his query: "disease=type 1 pneumonia" and "age=25". In search result A, disease=pneumonia, with respect to the query condition "disease=type 1 pneumonia", it has a similarity of 10% with that condition; age=21-30, with respect to the query condition "age=25", it has a similarity of 20% with that condition. Therefore, the average similarity is (10%+20%) 12=15%.

Thus, with the returned average similarity, the searching user can determine how approximately the search result can reflect his expectation, and determine whether this search result is what he needs in conjunction with other conditions.

Optionally, when returning search results to a searching user, those search results are sorted by average similarity. Thereby, the searching user can check the most similar result at first, improving checking efficiency consequently.

Alternatively, when returning a search result to a searching user, a weighted average similarity of that search result is returned to the searching user, wherein the weighted average similarity is the average of similarity values between that search result and each of the query conditions weighted by weights corresponding to those query conditions.

Referring to the above example again, if the searching user has specified a weight 60% to the query condition "disease=type 1 pneumonia", and a weight 40% to the query condition "age=25", then the weighted average similarity is 10%*60%+20%*40%=14%.

Optionally, when returning search results to a searching user, those search results are sorted by weighted average similarity.

Figure 4:
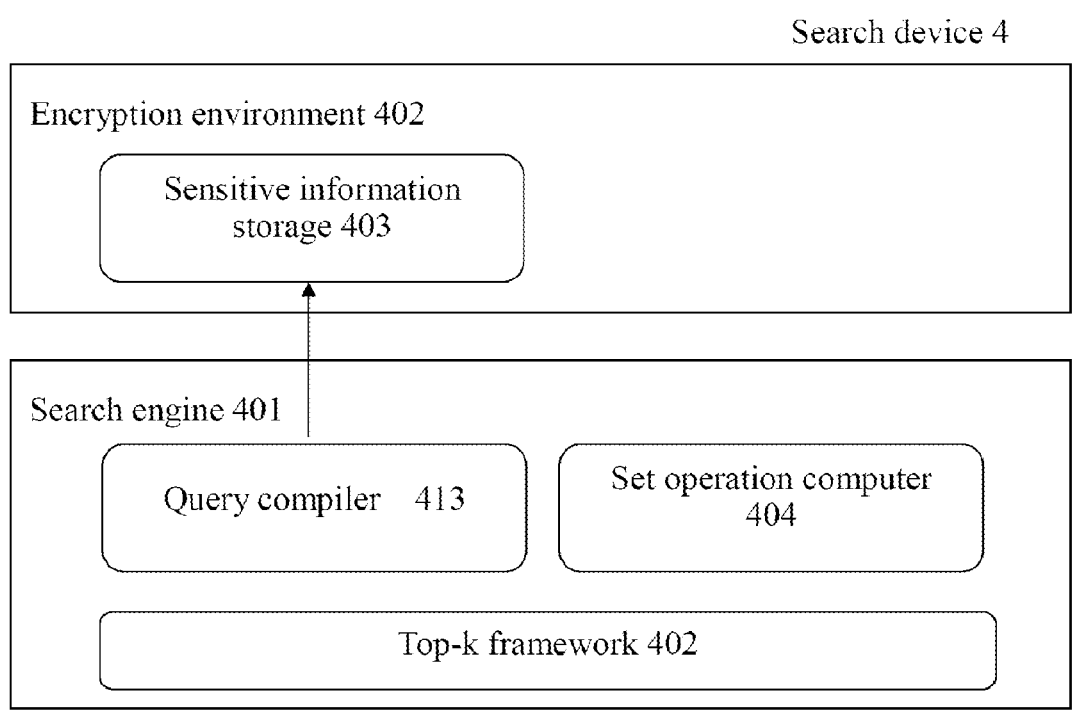
FIG. 4 shows a block diagram of a general search device.

FIG. 4 shows a block diagram of a general search device. As described in DESCRIPTION OF THE RELATED ART, the general search device implements secured search through secure operations, such as encryption. Search device 4 includes encryption environment 402 and search engine 401. Encryption environment 402 includes sensitive information storage 403. Search engine 401 includes Top-K framework 402, query compiler 413, and set operation computer 404.

For example, a certain kind of Top-K framework 402 receives a query containing some query conditions from a searching user, and sends the query conditions to query compiler 413 to translate them into SQL statements. Query compiler 413 queries sensitive information storage 403 with these SQL statements. Since a query from a searching user can include multiple query conditions, set operation computer 404 is required to merge the results acquired by query compiler 413 against each condition, and return them to the Top-K framework 402 to score the search results and set a score threshold. When the number of search results having scores higher than the threshold is less than K, Top-K framework 402 adjusts the threshold until the number of search results having scores higher than the threshold is larger than K, K is a nature number.

Figure 5:
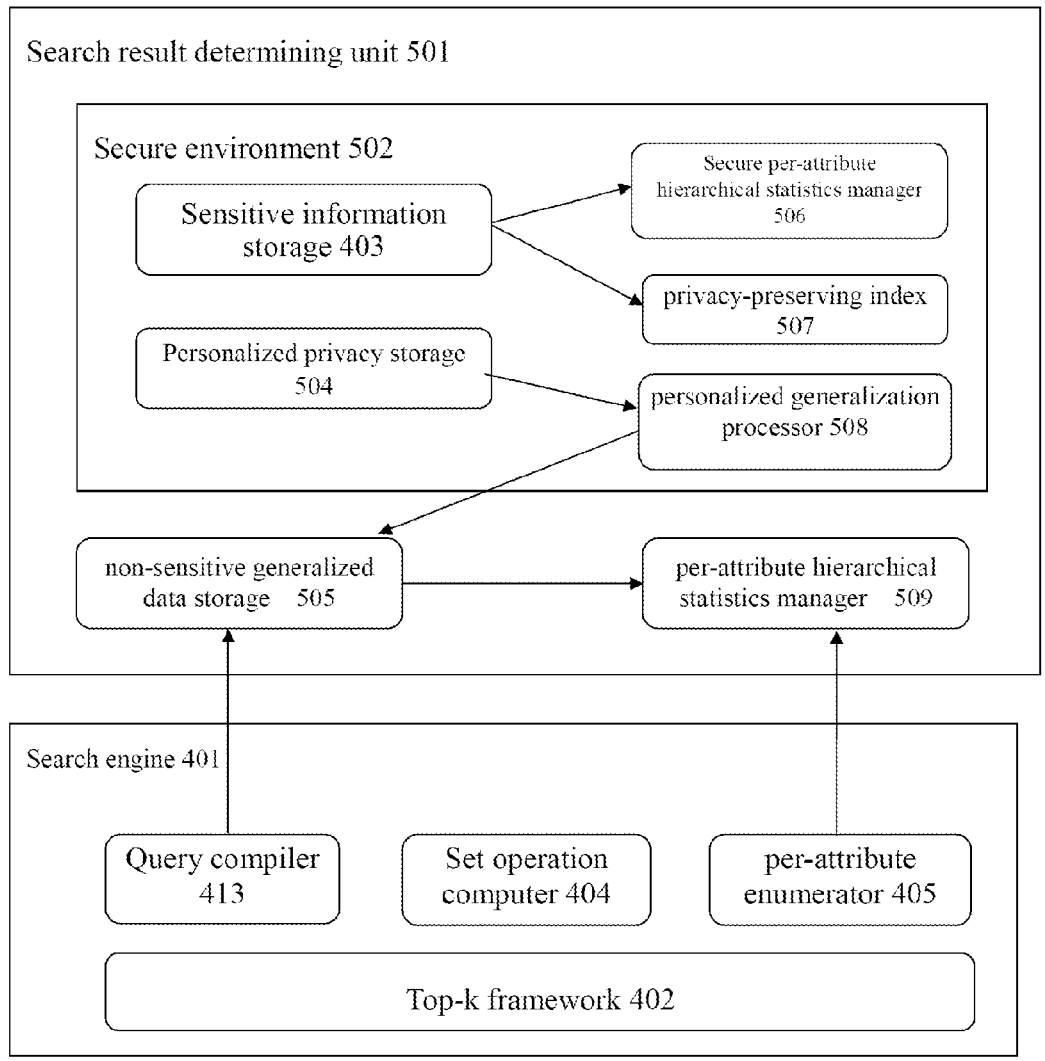
FIG. 5 shows a block diagram of a secured search device according to an embodiment of the present invention.

FIG. 5 shows a block diagram of a secured search device according to a first embodiment of the present invention. Secured search device 5 includes: search engine 401 configured to receive a search request from a searching user; and search result determining unit 501 configured to determine search results to be returned to the searching user based on a security schema. Search engine 401 is further configured to return the search results determined by search result determining unit 501 to the searching user.

Optionally, search result determining unit 501 is configured to generalize a value of an attribute in a tuple of a search result to form a search result to be returned to the searching user.

Optionally, search result determining unit 501 is configured to transform a value of an attribute in a tuple of a search result into a generalized value based on a privacy ratio, wherein the value of the attribute is a subclasses of the generalized value, and the ratio of the probability of finding original tuples based on a generalized value and the probability of finding original tuples based on a value of an attribute is less than or equal to the privacy ratio.

Search result determining unit 501 includes secure environment 502, which includes sensitive information storage 403, personalized privacy storage 504, secure per-attribute hierarchical statistics manager 506, privacy-preserving index 507, and personalized generalization processor 508. Furthermore, search result determining unit 501 includes non-sensitive generalized data storage 505 and per-attribute hierarchical statistics manager 509.

Search engine 401 includes query compiler 413, set operation computer 404, per-attribute enumerator 405 and Top-K framework 402.

Personalized privacy storage 504, secure per-attribute hierarchical statistics manager 506, privacy-preserving index 507, personalized generalization processor 508, non-sensitive generalized data storage 505, per-attribute hierarchical statistics manager 509, and per-attribute enumerator 405 are particular modules of embodiment 1, and other remaining modules have substantially the same functions as that in the prior art shown in FIG. 4.

Personalized privacy storage 504 is configured to store privacy ratios corresponding to each sensitive data in the sensitive information storage, which can have a similar storage format as that of sensitive information storage 403.

For example, sensitive information storage 403 stores the following content:

| name | Sex | age | Disease |
|---|---|---|---|
| A | Male | 25 | type 1 pneumonia |
| B | Female | 45 | emphysema |
| C | Male | 47 | type 2 pneumonia |
| D | Female | 67 | flu |

Consequently, personalized privacy storage 504 stores privacy ratios corresponding to each item:

| name | privacy ratio of Sex | privacy ratio of age | privacy ratio of disease |
|---|---|---|---|
| A | 100% | 100% | 50% |
| B | 100% | 50% | 100% |
| C | 100% | 100% | 34% |
| D | 100% | 34% | 100% |

Secure per-attribute hierarchical statistics manager 506 is configured to produce a coverage statistic of a value of an attribute based on the value of the attribute, wherein coverage means how many tuples have that attribute with that value or subclasses of that value in the sensitive information storage. For example, as to "disease=pneumonia", its coverage statistic is 2. As to "disease=pulmonary disease", its coverage statistic is 3.

Personalized generalization processor 508 is configured to pre-generalize sensitive information in the sensitive information storage according to the sensitive information stored in the sensitive information storage 403, the privacy ratios stored in the personalized privacy storage 504 and the coverage statistics of each value of attribute produced by the secure pre-attribute hierarchical statistics manager 506 to conform the privacy ratios stored in the personalized privacy storage, and then store the generalized information in non-sensitive generalized data storage 505.

With respect to data with 100% privacy ratio, those data can be directly copied into non-sensitive generalized data storage 505, since the owners of that data have no security requirements. As to sensitive data with privacy ratios rather than 100%, those data should be generalized into generalized data in a manner as described previously.

For example, as to the disease "type 1 pneumonia" of patient A, a privacy ratio of 50% desired by patient A is specified. Therefore, it is generalized to "pneumonia". In this way, the ratio of the 50% probability at which the specific tuple containing the original data "type 1 pneumonia" is found based on the generalized data "pneumonia" and the 100% probability at which the specific tuple is found based on the original data "type 1 pneumonia" is 50%, which is less than or equal to the 50% privacy ratio. Thus, non-sensitive generalized data storage 505 stores content:

| name | Sex | age | Disease |
|---|---|---|---|
| A | Male | 25 | pneumonia |
| B | Female | 41-50 | emphysema |
| C | Male | 47 | pulmonary disease |
| D | Female | 41 above | flu |

Privacy-preserving index 507 is an optional unit, which can speed up the implementation of the generalization of personalized generalization processor 508. Many techniques can be used to implement the privacy-preserving index, which will not be described in detail herein, since they are not necessary for the implementation of the present invention.

Per-attribute enumerator 405 enumerates hierarchical attribute values according to an attribute tree established from the generalized information stored in the non-sensitive generalized data storage. For example, as to the attribute "age", a hierarchical tree structure is constructed from age values "47"-"41-50"–"41 above". Per-attribute enumerator 405 then sends "47", "41-50", "41 above" to per-attribute hierarchical statistics manager 509, respectively.

Per-attribute hierarchical statistics manager 509 is configured to produce a coverage statistic of a value of an attribute based on the value of the attribute, wherein coverage means how many tuples have that attribute with that value or subclasses of that value in the non-sensitive generalized information storage. In the above example, coverage statistics 1, 2 and 3 are respectively produced in response to the enumeration "47", "41-50", "41 above" of per-attribute enumerator 405.

Per-attribute enumerator 405 calculates an average similarity or weighted average similarity of a search result based on the coverage statistics produced by the per-attribute hierarchical statistics manager, and then returns it to the searching user along with that search result. The average similarity or weighted average similarity is calculated as described above.

Optionally, search results are sorted by average similarity or weighted average similarity when they are returned to the searching user along with average similarity or weighted average similarity values.

Other parts of FIG. 5 are similar to that of FIG. 4.

The first embodiment described above is a static scheme, which is suitable to stable dataset without frequent updating for its larger cost for updating. Specifically, updating an original tuple can lead to the updates in the following four aspects: updating the sensitive tuple in sensitive information storage 403; updating the statistical results in secure pre-attribute hierarchical statistics manager 506; updating non-sensitive data in non-sensitive generalized data storage 505, wherein not only the update of a tuple corresponding to the updated tuple in sensitive information storage 403, but also other necessary updates caused by the changes in non-sensitive generalized data storage 505 leading to specific unsatisfied privacy ratios by some generalized data in the statistical results of pre-attribute hierarchical statistics manager 506 should be considered; updating the statistical results in per-attribute hierarchical statistics manager 509.

Taking the insertion of an original tuple as an example, first, it must be inserted into sensitive information storage 403. The coverage statistics generated per attribute in secure pre-attribute hierarchical statistics manager 506 are changed inevitably due to the change in the original tuples stored in sensitive information storage 403. Therefore, secure pre-attribute hierarchical statistics manager 506 needs to re-produce coverage statistics of values of each related attribute. Nevertheless, it is required to update non-sensitive data in non-sensitive generalized data storage 505. In doing so, a tuple corresponding to the tuple added in sensitive information storage 403 should be inserted in non-sensitive generalized data storage 505, wherein, in the tuple added in non-sensitive generalized data storage 505, original sensitive data is substituted with generalized data based on the privacy ratios. In addition, due to the change in the coverage statistics of the values of each attribute generated by secure pre-attribute hierarchical statistics manager 506, some generalized data in non-sensitive generalized data storage 505 can not meet their privacy ratio requirements based on the coverage statistics of the newly updated values of each attribute as they did based on the coverage statistics of their original values of each attribute, any more. Thus, a plenty of generalized data in non-sensitive generalized data storage 505 need to be updated. Finally, due to the updating of a plenty of generalized data in non-sensitive generalized data storage 505, the coverage statistics of the values of each attribute in turn need to be re-generated in per-attribute hierarchical statistics manager 509.

Therefore, the static scheme of the first embodiment has higher updating cost, in which, generally, periodical updating is suitable, namely, the above updating process is carried out one time only if a certain amount of updates of the original tuples have been accumulated.

Privacy-preserving index 507 can be used to maintain update condition.

Figure 6:
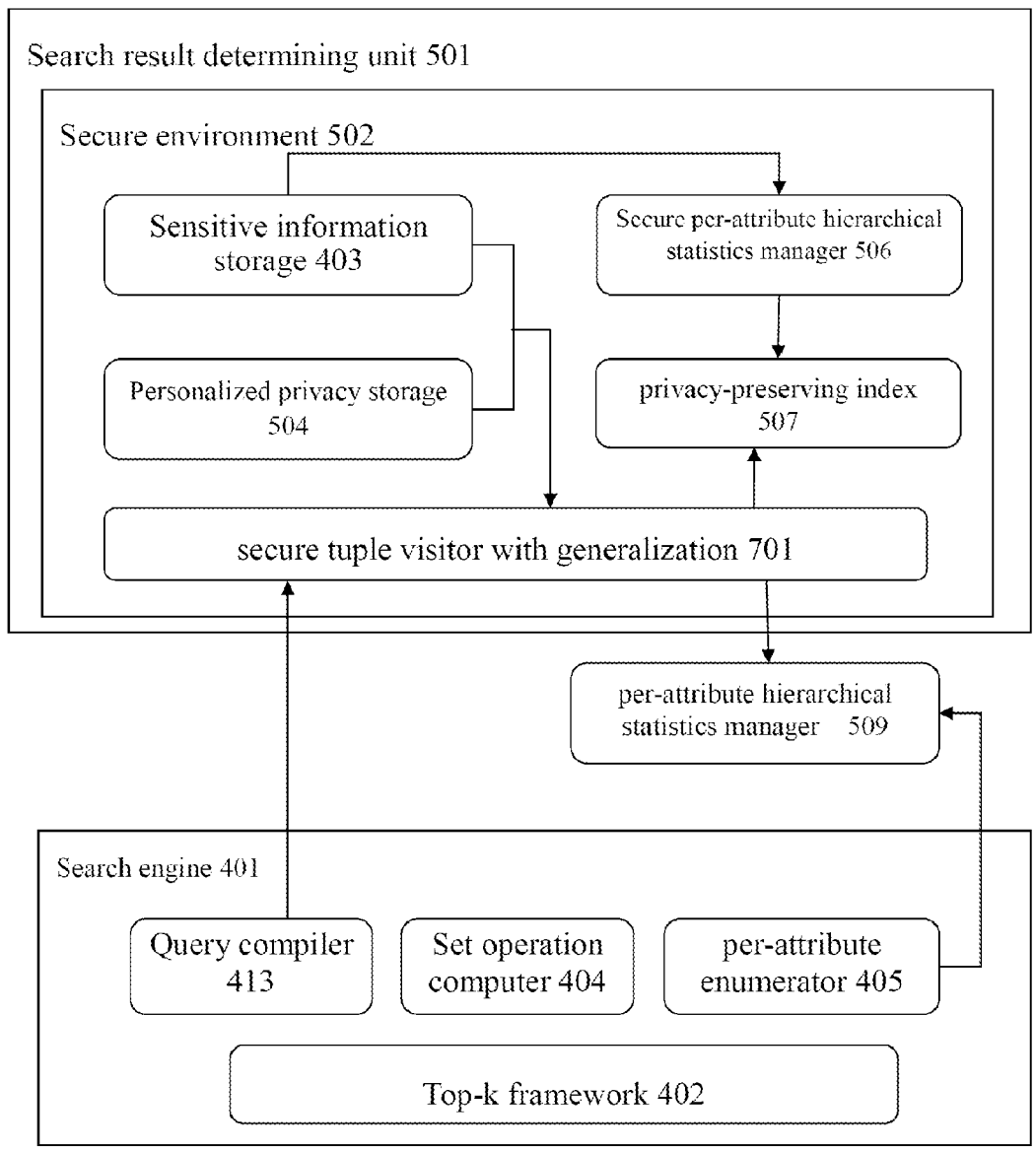
FIG. 6 shows a block diagram of a secured search device according to another embodiment of the present invention.

FIG. 6 shows a block diagram of a secure device according to a second embodiment of the present invention. Unlike the first embodiment, the second embodiment is an embodiment of a dynamic scheme suitable for dataset with frequent modification. Instead of maintaining a secured version of data as that in the first embodiment, in the second embodiment, query is implemented on original data and generalization is carried out at the same time.

The difference between the second embodiment of FIG. 6 and the first embodiment of FIG. 5 lies that non-sensitive generalized data storage 505 is cancelled and personalized generalization processor 508 is substituted by secure tuple visitor with generalization 701.

After translating a query of a searching user into SQL statements, query compiler 413 sends those SQL statements to secure tuple visitor with generalization 701 directly. In response to each query, secure tuple visitor with generalization 701 directly queries the original sensitive information in sensitive information storage 403, and then generalize the values of attribute in the original tuples corresponding to the query to generalized values according to sensitive information stored in the sensitive information storage, the privacy ratios stored in the personalized privacy storage and the coverage statistics of the values of each attribute in the secure pre-attribute hierarchical statistics manager in a manner similar to that of personalized generalization processor 508 of FIG. 5.

It can be seen that, in the second embodiment, instead of implementing generalization in advance, secure tuple visitor with generalization 701 implements generalization in response to each query. Hence, as for updating, only the updating of the sensitive tuples in sensitive information storage 403 and the updating of the statistical results in secure pre-attribute hierarchical statistics manager 506 need to be considered. Updating cost can be significantly reduced, for no generalized data update, or coverage statistic re-calculation of each attribute value is involved in the case of a lot of changes in the generalized data, with a negative effect of slower response to each query. For the expense of search efficiency, this method can realize lower updating cost and is suitable for data with frequent modification. For data with frequent modification, if updating is implemented periodically as that in the first embodiment, it should be implemented in a shorter period of time in order to avoid the inaccuracy of statistical data, leading to a remarkable problem of updating cost; for data without frequent modification, the problem of updating cost is not critical due to the long period of updating time.

Per-attribute enumerator 405 of FIG. 6 enumerates the values of an attribute according to the search results. For example, given a user queries "disease=type 1 pneumonia" and a search result "patient A, male, 25, pneumonia", "disease=pneumonia" is enumerated by per-attribute enumerator 405, and is sent to per-attribute hierarchical statistics manager 509. Per-attribute hierarchical statistics manager 509 generates the coverage statistics of the attribute values enumerated by the per-attribute enumerator, where the coverage statistics represents how many tuples in the history of generalized values generalized by the secure tuple visitor with generalization have the attribute with such a value or subclasses of the value. The history of generalized data generalized by the secure tuple visitor with generalization can be obtained through privacy-preserving index 507.

There are many existing techniques to achieve privacy-preserving index 507.

Per-attribute enumerator 405 calculates an average similarity or weighted average similarity of a search result according to the coverage statistics generated by the per-attribute hierarchical statistics manager 509 and returns it to the searching user along with the search result.

Optionally, the search results are sorted by average similarity or weighted average similarity when the average similarity or weighted average similarity values of search results are returned to the searching user along with those search results.

Other parts of FIG. 6 are similar to FIG. 5.

In one embodiment of the present invention, a computer device is further provided, which includes the secured search device of FIG. 5 or FIG. 6.

Figure 7:
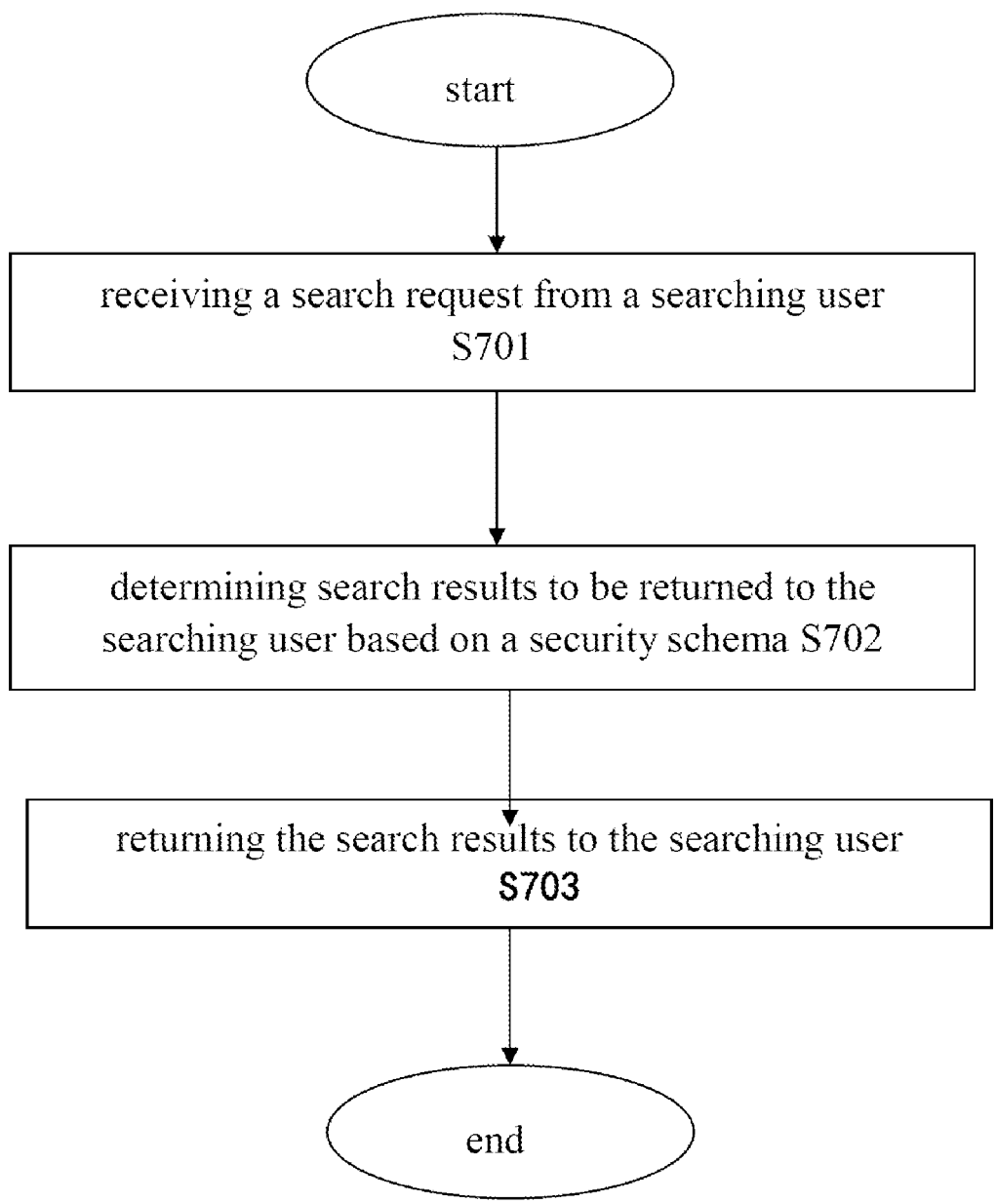
FIG. 7 shows a block diagram of a method according to an embodiment of the present invention.

FIG. 7 shows a block diagram of a method for an embodiment of the present invention. In this embodiment, the secured search method includes: at step S701, receiving a search request from a searching user; at step S702, determining search results to be returned to the searching user based on a security schema; and at step S703, returning the search results to the searching user.

As will be appreciated by one skilled in the art, aspects of the present invention can be embodied as a system, method or computer program product. Accordingly, aspects of the present invention can take the form of an entirely hardware embodiment, an entirely software embodiment (including firmware, resident software, microcode, etc.) or an embodiment combining software and hardware aspects that can all generally be referred to herein as a "circuit," "module," "unit," or "system." Furthermore, aspects of the present invention can take the form of a computer program product embodied in any tangible medium of expression having computer usable program code embodied therein.

Any combination of one or more computer usable or computer readable medium(s) can be utilized. The computer usable or computer readable medium can be, for example, but not limited to, an electronic, magnetic, optical, electromagnetic, infrared, or semiconductor system, apparatus, device, or propagation medium. More specific examples (a non-exhaustive list) of the computer readable medium can include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium supporting for example the Internet or Intranet, or a magnetic storage device. Note that the computer usable or computer readable medium even can be paper or other suitable medium on which programs are printed, and this is because the programs can be obtained electronically by electrically scanning the paper or other medium, and then be compiled, interpreted or processed appropriately, and be stored in a computer memory if necessary. In the context of this document, a computer usable or computer readable storage medium can be any medium that contains, stores, communicates, propagates, or transmits a program for use by or in connection with an instruction execution system, apparatus, or device. A computer useable medium can include a data signal with computer usable program code embodied therein, propagated in baseband or as part of a carrier wave. The computer usable program code can be transmitted using any appropriate medium, including but not limited to wireless, wireline, optical fiber cable, RF, etc.

Computer program code for carrying out operations for aspects of the present invention can be written in any combination of one or more programming languages, including an object oriented programming language such as Java, Smalltalk, C++ or the like and conventional procedural programming languages, such as the "C" programming language or similar programming languages. The program code can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions can be provided to a processor of a general purpose computer, special purpose computer, or other programmable data processing apparatus to produce a machine, such that the instructions, which execute via the computer or other programmable data processing apparatus, create means for implementing the functions/acts specified in the blocks of the flowchart illustrations and/or block diagrams.

These computer program instructions can also be stored in a computer readable medium that can direct a computer or other programmable data processing apparatus to function in a particular manner, such that the instructions stored in the computer readable medium produce an article of manufacture including instruction means which implement the functions/acts specified in the blocks of the flowchart illustrations and/or block diagrams.

The computer program instructions can also be loaded onto a computer or other programmable data processing apparatus to cause a series of operational steps to be performed on the computer or other programmable data processing apparatus to produce a computer implemented process such that the instructions which execute on the computer or other programmable apparatus provide processes for implementing the functions/acts specified in the blocks of the flowchart illustrations and/or block diagrams.

The flowchart illustrations and block diagrams in the figures illustrate the architecture, functionality, and operation of possible implementations of systems, methods and computer program products according to various embodiments of the present invention. In this regard, each block in the flowchart illustrations or block diagrams can represent a unit, module, program segment, or portion of code, which includes one or more executable instructions for implementing the specified logical function(s). It should also be noted that, in some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable those of ordinary skill in the art to understand the invention for various embodiments with various modifications as are suited to the particular use contemplated.

What is claimed is:

1. A method for secured search, comprising the steps of:
receiving a search request from a searching user;
determining an ungeneralized first search result which is:
(i) responsive to the search request, and (ii) in the form of a tuple that includes a plurality of attributes values respectively corresponding to an ordered set of attributes;
for each ordered attribute of the ungeneralized first search result, determining a privacy ratio for the ordered attribute where two, or more, of the privacy ratios are unique;
for each attribute value of the ungeneralized first search result, generalizing the attribute value based on the respectively associated privacy ratio for the ordered attribute corresponding to the attribute value to convert the ungeneralized first search result into a generalized first search result; and
returning the first generalized search result to said searching user,
wherein:
at least one of the steps is carried out by using a computer device.

2. The method of claim 1, wherein each respectively associated privacy ratio for each ordered attribute is unique.

3. The method of claim 1, wherein two, or more, of the privacy ratios are the same.

4. The method of claim 1, wherein the ungeneralized first search result is in the form of a plurality of tuples, each tuple of the plurality of tuples includes a plurality of attributes values respectively corresponding to an ordered set of attributes.

5. The method of claim 4, wherein the privacy ratio for respective attributes of the plurality of tuples is unique.

6. A computer program product for secured search, the computer program product comprising a non-transitory computer readable storage medium having stored thereon:
- first program instructions programmed to receive a search request from a searching user;
- second program instructions programmed to determine an ungeneralized first search result which is: (i) responsive to the search request, and (ii) in the form of a tuple that includes a plurality of attributes values respectively corresponding to an ordered set of attributes;
- third program instructions programmed to, for each ordered attribute of the ungeneralized first search result, determine a privacy ratio for the ordered attribute where two, or more, of the privacy ratios are unique;
- fourth program instructions programmed to, for each attribute value of the ungeneralized first search result, generalize the attribute value based on the respectively associated privacy ratio for the ordered attribute corresponding to the attribute value to convert the ungeneralized first search result into a generalized first search result; and
- fifth program instructions programmed to return the first generalized search result to said searching user.

7. The computer program product of claim 6, wherein each respectively associated privacy ratio for each ordered attribute is unique.

8. The computer program product of claim 6, wherein two, or more, of the privacy ratios are the same.

9. The computer program product of claim 6, wherein the ungeneralized first search result is in the form of a plurality of tuples, each tuple of the plurality of tuples includes a plurality of attributes values respectively corresponding to an ordered set of attributes.

10. The computer program product of claim 9, wherein the privacy ratio for respective attributes of the plurality of tuples is unique.

11. A computer system for secured search, the computer system comprising:
- a processor(s) set; and
- a computer readable storage medium;
- wherein:
  - the processor set is structured, located, connected and/or programmed to run program instructions stored on the computer readable storage medium; and
  - the program instructions include:
    - first program instructions programmed to receive a search request from a searching user;
    - second program instructions programmed to determine an ungeneralized first search result which is: (i) responsive to the search request, and (ii) in the form of a tuple that includes a plurality of attributes values respectively corresponding to an ordered set of attributes;
    - third program instructions programmed to, for each ordered attribute of the ungeneralized first search result, determine a privacy ratio for the ordered attribute where two, or more, of the privacy ratios are unique;
    - fourth program instructions programmed to, for each attribute value of the ungeneralized first search result, generalize the attribute value based on the respectively associated privacy ratio for the ordered attribute corresponding to the attribute value to convert the ungeneralized first search result into a generalized first search result; and
    - fifth program instructions programmed to return the first generalized search result to said searching user.

12. The computer system of claim 11, wherein each respectively associated privacy ratio for each ordered attribute is unique.

13. The computer system of claim 11, wherein two, or more, of the privacy ratios are the same.

14. The computer system of claim 11, wherein the ungeneralized first search result is in the form of a plurality of tuples, each tuple of the plurality of tuples includes a plurality of attributes values respectively corresponding to an ordered set of attributes.

15. The computer system of claim 14, wherein the privacy ratio for respective attributes of the plurality of tuples is unique.

* * * * *